United States Patent [19]

Collombel et al.

[11] Patent Number: 5,166,187

[45] Date of Patent: Nov. 24, 1992

[54] BIOMATERIALS WITH A BASE OF MIXTURES OF COLLAGEN, CHITOSAN AND GLYCOSAMINOGLYCANS, PROCESS FOR PREPARING THEM AND THEIR APPLICATION IN HUMAN MEDICINE

[75] Inventors: Christian Collombel, Lyon; Odile Damour, Saint Genis Laval; Christian Gagnieu; Frederique Poinsignon, both of Lyon; Christian Echinard, Gemenos; Jacques Marichy, Lyon, all of France

[73] Assignee: Centre National De La Recherche, Paris, France

[21] Appl. No.: 314,508

[22] Filed: Feb. 15, 1989

Related U.S. Application Data

[63] Continuation of PCT/FR88/00303, Jun. 14, 1988.

[30] Foreign Application Priority Data

Jun. 15, 1987 [FR] France .............................. 87 08752

[51] Int. Cl.$^5$ ............................................ A61K 37/12
[52] U.S. Cl. ...................................... 514/21; 530/356
[58] Field of Search ............................ 514/21; 530/356

[56] References Cited

U.S. PATENT DOCUMENTS

4,378,017  3/1983  Kosugi et al.
4,448,718  5/1984  Yannas et al. ........................ 530/409
4,784,986  11/1988  Usher ................................. 530/356
4,808,570  2/1989  Michaeli ................................. 514/2

FOREIGN PATENT DOCUMENTS

0089157  9/1983  European Pat. Off.
0138385  4/1985  European Pat. Off.
0200574  5/1986  European Pat. Off.

*Primary Examiner*—John Doll
*Assistant Examiner*—Choon P. Koh
*Attorney, Agent, or Firm*—Browdy and Neimark

[57] ABSTRACT

This biomaterial comprises at least a compound consisting of an association of collagen, chitosan acetylated to a degree of acetylation between about 10 and about 40% and of glycosaminoglycans.

It has its application in orthopedics and plastic surgery and for making extracellular matrices for regeneration of nerve cells and bones as well as biocompatible envelopes.

A particular application is the making of artificial skin consisting of a dermal layer of the velvet type obtained from biomaterials such as those described above.

The process of obtaining this dermal layer consists in adding a collagen solution of the chitosan, then in adding to the collagen-chitosan a mixture of chondroitins 4- and 6-sulfate.

18 Claims, 3 Drawing Sheets

BIOMATERIALS WITH A BASE OF MIXTURES OF COLLAGEN, CHITOSAN AND GLYCOSAMINOGLYCANS, PROCESS FOR PREPARING THEM AND THEIR APPLICATION IN HUMAN MEDICINE

This is a continuation of application PCT/FR88/00303, the international filing date of which is Jun. 14, 1988.

FIELD OF THE INVENTION

This invention relates to new biomaterials with a base of mixtures of collagen, chitosan and glycosaminoglycans, a process for preparing them and their application, particularly in dermatology and for covering burns and in plastic surgery.

BACKGROUND OF THE INVENTION

According to the invention, these new biomaterials are characterized in that they comprise at least one compound consisting of an association of collagen, chitosan and glycosaminoglycans.

Chitosan, preferably obtained by simple deacetylation of chitin, remains acetylated at a degree of acetylation between about 10% and about 40%.

The biomaterials according to the invention can be used in all losses of substance and for reconstitution of all tissues.

Actually, all the physical characteristics (resistance, elasticity, size of pores, degradation time...) can be modified and adapted to the planned use by acting on the proportion of the various constituents.

When implanted, the extracellular matrix constituted by this biomaterial will be colonized by adequate cells which will reconstitute IN VIVO the tissue which is specific to them.

Thus, osteoblasts will synthesize a connective tissue which will calcify to give bone. Fibroblasts will give connective tissues (dermes, arteries...) and nerve cells, nerves.

This invention will first be described in one of its most important applications which is artificial skin allowing the simultaneous reconstitution of the dermis and epidermis, while avoiding the formation of hypertrophic cicatrices.

This entirely biodegradable artificial skin, will be used mainly for early covering of burns after early excision of cutaneous wounds of man and animals.

It is known that in the case of deep, extensive burns, it is essential to reconstruct as fast and lasting as possible an impermeable cutaneous barrier, on the one hand, to protect the burns from infection and calorico-nitrogen losses, on the other hand, the dermis acts as a mold to avoid hypertrophic cicatrices and retractions due to anarchic proliferation of fibroblasts.

Allographs are expensive and do not constitute an effective covering, because they are very often rejected, which causes additional shock for the patients.

The standard techniques of autograph are feasible only in the case of moderately extensive burns.

The progress of medico-surgical intensive care now makes it possible to keep burned patients alive with 80% of the cutaneous surface burned. This progress has resulted in increasing the need for skin or skin equivalent.

Numerous studies have been undertaken for this purpose.

Thus Green and O'Connor aimed at reconstituting the epidermis from keratocytes coming from the cells of the patient.

Bell and his team developed a skin equivalent consisting of a dermal layer of autologous fibroblasts and bovine collagen and an epidermal layer of autologous keratinocytes.

It should be noted that use of these two techniques requires a waiting time of twenty-one days (corresponding to the culture period of the cells) before being able to have artificial skin suitable for the patient.

A third technique was developed by Yannas and Burke (Jal of Biomedical Materials Research, Vol. 14, 65-81, 107-131, 511-528 (1980) and FR-A- 2 332 863).

The artificial skin proposed by these authors comprises two layers:

a dermal equivalent consisting of calf collagen and a glycosaminoglycans (GAG), chondroitin 6-sulfate, and crosslinked by glutaraldhyde;

a temporary pseudoepidermis of nonbiodegradable silicone resin limiting the exudative losses of the early phase and acting as a barrier to infectious agents, coming to cover the dermal layer.

This artificial skin is put in place after early excision of the third degree burned tissue (48 and 72 hours after burning). The collagen-GAG contains pores through which the endogenous neodermis in a way is "channeled." Thus, a "domestic" cicatricial tissue, very close to the normal dermis, is reconstituted, and at whose level the synthesis of collagen by fibroblasts does not occur in an anarchic manner unlike the tissue of usual granulation. When the dermal layer is revascularized (3 to 4 weeks), and when epidermal cells are deposited, *the silicone membrane is removed.* Then a extremely thin epidermal graft, as fillet 4 or 9, (taken from remaining donor areas) is put in place.

This process of cutaneous covering after early excision, already tested in the USA on more than two hundred burn patients, in five centers, proves to be particularly effective both in combating hydric and calorico-nitrogen exudative losses of the early phase and in preventing infection and to reduce the magnitude of the hypertrophic and retractile sequellae.

This compact, crosslinked matrix is colonized by fibroblasts of the wounded person which synthesize their own collagen and all the human proteins necessary for reconstitution of the connective tissue.

The degradation time of the artificial dermis, which is twenty four days, corresponds to the time of healing of the wound.

Thus channeled, the fibroblasts of the burned patent can take a good orientation, which avoid hydrotrophic cicatrices.

It remains, of course, to epidermize in a second period.

This material meets emergency needs. It can be sterilized and stored in large amounts.

This technique, advantageous though it may be, still has several drawbacks, both in regard to the dermis and the pseudoepedermis.

For the dermis:

The association of the collagen and glycosaminoglycans described by YANNAS and BURKE give composite materials in which the constituents are easily dissociable particularly because of the poverty of the collagen in ionizable basic functions. These composite materials are soluble in the liquids of the organism and should be crosslinked at the level of the collagen for their use in aqueous medium to be possible. However, the slight cohesion between crosslinked collagen and acid glycosaminoglycans is responsible for a progressive salting out of the GAGs each time an immersion in an aqueous solution is necessary (hydration, washing, neutralization, etc...). Salting out, which is difficult to control, considerably modifies the final composition of the dermes.

To reduce its degradation, to increase its resistance, it is necessary to crosslink the collagen-GAG coprecipitate, either by chemical crosslinking by using glutaraldehyde, a product toxic to the organism, which requires, on the one hand, elimination of the excess glutaraldehyde and, on the other hand, control of its elimination of the finished product by physical crosslinking by the simultaneous action of heat and vacuum.

For the pseudoepidermis:

The pseudoepidermis of silicone resin is not biodegradable. Therefore it is necessary to remove it surgically before epidermizing.

Moreover, it cannot be used as a support of in vitro and in vivo culture.

The most recent technique is that proposed by WIDRA (EP-A-0 089 152 and EP-A-0 138 385), who proposes an artificial skin made from the association of anionic compounds derived from keratin and cationic biopolymers such as chitosan and collaqen.

These compounds can be applied in two staqes to form, IN SITU, a hydrogel membrane which forms a protective carapace and, at the end of cicatrization, hardens and falls off.

SUMMARY OF THE INVENTION

In the present invention, the inventors have aimed at preparing a new artificial skin not exhibiting the drawbacks of the techniques mentioned above. For this purpose, they established certain criteria that the dermis and epidermis should meet.

The dermis, of course, should:

facilitate the migration of fibroblasts and endothelial cells,
exhibit little or no antigenicity,
degrade at a controllable rate,
make it possible to reduce and prevent contractures,
activate the cicatrization and prevent infection,
not cause inflammatory reaction,
reduce pain,
prevent hydrotrophic cicatrices.

Further, it should be well tolerated, be resistant and able to be handled without it being necessary to resort to a crosslinking of the constituents.

The epidermis should be completely biodegradable and able to serve as a cell culture support; further, it should be impermeable to bacteria, regulate the liquid flow and exhibit pores of controlled dimensions.

The artificial skin according to the invention is characterized in that it consists essentially of a dermal layer of the velvet type comprising the association of collagens, chitosan, chrondioctins 6- and 4-sulfate and optionally of hyaluronic acid. This dermal layer is associated with a biodegradable pseudoepidermis with a membraned structure.

The composition of the dermal layer according to the invention is entirely original. It is known that the addition of polyanionic or polycationic molecules to collagen leads to the formation to ionic networks in which either amine groups or carboxyl groups of this protein intervene. The density of these bonds in the composite materials obtained depends on the accessibility of these groups, their distribution and their number.

Complexes associating collagen and chitosan already exist. Thus, KOSUGI and KOTTO (US-A-4378017) prepare fibrous bovine collagen—crab macrobibrillar chitosan that can be used in the food industry. It is an acetytchitosan whose degree of acetylation is preferably between 0 and 30%. This material causes ionic bonds to intervene among its constituents but they seem totally insufficient to affect its stability and its rigidity. It is essential to resort to a chemical crosslinking to stabilize the complex. The membranes obtained by the authors are transparent, very resistant to traction, elastic and thermostable. Moreover, they are insoluble in water and in an acid medium in contrast with the initial collagen and chitosan taken separately. However, these membranes are hydratable in an aqueous medium without salting out of the constituents occurring and give flexible, homogeneous structures whose physico- chemical and biological properties are compatible with their optional use as cell culture support.

In this case, only the carboxyl groups of the collagen intervene in the formation of the network.

EP-A-200 574 describes a biomaterial made up of atelocollagen, N-acylchitosan and optionally chondroitin sulfate.

The N-acylchitosan described here in this document is obtained by a two-stage process. The first of these stages consists of deacetylation to at least 55% and preferably 70 to 100% of the chitin. The second stage consists of a reacylation of the chitosan obtained, particularly with acetic or succinic acid, up to a acylation equal to at least 55%, but preferably between 70 and 100%.

This acylchitosan is acylated to a acylation degree at least equal to 55% but preferably between 70 and 100%.

Now, at acylation to at least 77% but preferably between 70 and 100% means that the acylchitosan exhibits, at most, 45% free $NH^{3}+$ amine functions. This limits the possibilities of bonding of these amine functions with $COO^-$ of collagen or $SO_4^{--}$ and $COO^{--}$ groups of chondroitins sulfate, according to the following diagram:

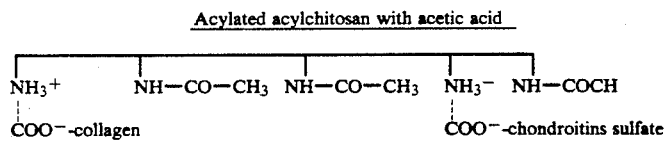

The number of ionic bonds between constituents therefore is relatively slight and the ionic network is much smaller.

Thus, as EP-A-200 574 specifies, it is preferable to resort to a chemical crosslinking process (use of hexamethylene diiisocyanate or glutaraldehyde) to increase sufficiently the resistance and absorption capacity in water and to prevent salting out of the glycosaminoglycans.

In case the acylation is performed with a diacid such as succinic acid, this causes an increase in the number of COO⁻ carboxyl functions which are bonded, intramolecularly, with NH₃⁺ amine functions of the succinylchitosan itself and intramolecularly with the NH₃⁺ amine functions of another chain of succinylchitosan or collagen.

Therefore there remain less free NH₃⁻ amine functions able to be bonded with acid groups of collagen and/or of glycosaminoglycans. We have

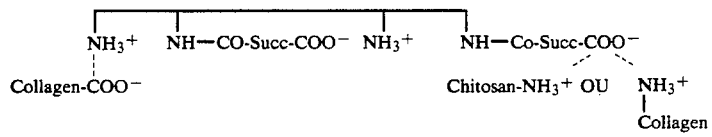

Further, the biomaterial obtained according to the teaching of this document should be chemically crosslinked to be of the correct quality.

The inventors have discovered that it was possible to obtain quite exceptional results by forming ionic networks in which both carboxyl groups and collagen amine groups intervene.

The simultaneous participation of these two ionizable groups is obtained by associating the collagen With both chondroitin sulfates and chitosan. The structure obtained is stabilized by the formation of ionic bonds between acid functions of chondroitins sulfate and chitosan amine functions.

This association makes possible the formation of ionic networks in which both carboxyl and amine collagen groups intervene which, respectively, are bonded to the chitosan amine functions exhibiting a slight rate of residual acetylation and to sulfate and carboxyl groups of the chondroitins 4- and 6-sulfate. Further, the acid and sulfate groups of chondroitins 4- and 6-sulfate can be ionically bonded to the chitosan amine functions.

The cohesion of these ionic networks is strong enough for the dermis to be insoluble in an aqueous medium and for no salting out of the chondroitins sulfate to exist. This stability which is reflected in particular by the absence of chondroitins sulfate makes it possible to avoid use of the usual crosslinking processes by covalent bonds (glutaraldehyde, acid azide, diisocyanates...).

The major constituent of the dermal layer according to the invention is collagen, and preferably type I+III collagen, native or without telopeptides with preserved helicoid structure, whether collagen of human origin, placenta extract or bovine collagen is involved. This collagen soluble in the fluids of the organism is entirely degradable by the cellular enzymes and is perfectly tolerated by the human organism.

Chitosan (polyglycosamine) is the second component of the dermis according to the invention. This chitosan can have different origins.

As mentioned above, it is obtained in a single stage by N-deacetylation of microfibrillar chitosan (poly-N-acetylglucosamine) with of shrimp carapaces. This aminopolyoside exhibits a high power of absorption of proteins rich in amino acids (glutamic and aspartic acids).

The speed of enzymatic degradation of the chitosan is a function both of its molecular weight and its degree of acetylation. The chitosan going into the composition of the dermes, object of the invention, exhibits an average molecular weight between 150,000 and 1,000,000 and degrees of acetylation between 40 and 10%. This acetylation rate constitutes an essential difference from the materials of the prior art described above; actually, the acylchitosan according to the invention exhibits enough free amine groups for it to be bonded both to the collagen and to the glycosaminoglycans. The variation in the molecular weight and the degrees of acetylation make it possible to modify the cohesion of the constituents of the dermes and thus to modulate their biological and physicochemical properties as a function of the desired ends.

Further, the chitosan exhibits interesting biological properties that can be used clinically. It is hemostatic and cicatrizing and can be used as a cell culture support. Its role of protection of the animal organism in regard to bacterial and fungal infections was also demonstrated. It acts by stimulation of the immune system and, in particular, it induces the activation of macrophages. This property has been used in animals in the treatment of cancerous tumors.

Chitosan and the collagen-chitosan composite therefore exhibit physicochemical and biological properties compatible with their use as a constituent of artificial dermes.

The 3rd and 4th constituents, the chondroitins sulfate and hyaluronic acid are glycosaminoglycans.

Glycosaminoglycans are an integral part of the connective tissue.

Glycosaminoglycans are characterized by linear disaccharide units, generally consisting of a uronic acid (glucuronic acid or iduronic acid) and a hexosamine (glucosamine or glactosamine) very often N-acylated and esterified by sulfuric acid.

The main glycosaminoglycans are:
hyaluronic acid,
chondroitin 4-sulfate or chondroitin sulfate A (CSA),
chondroitin 6-sulfate or chondroitin sulfate C (CSC),
dermatane sulfate or chondroitin sulfate B (CSB),
heparan sulfate (HS),
keratan sulfate (KS) which differ from other glycosaminoglycans by the presence of galactose instead of uronic acid.

The chondroitins 4- and 6-sulfate are the most common. They are polymers whose basic unit is the following: glucuronyl (beta 1,3)N-acetylgalactosamine sulfate (beta 1,4). The chondroitins 4- and 6-sulfate differ only by their position on the sulfate group. The galactosamine molecule is esterified either in the 4 position (chondroitin 4-sulfate or chrondrotin sulfate A) or in the 6 position (chondroitin 6-sulfate or chondroitin sulfate C).

It was shown that sulfated glycosaminoglycans, with the exception of keratan sulfate, could form, in vitro and at physiological pHs, ionic bonds with the collagen. These bonds are stronger the higher the iduronic acid content of the glycosaminoglycan.

The coprecipitation of the collagen and of the chondroitin 6-sulfate at acid pH slows the degradation of the collagen by masking the collagenase action site and reduces its immunogenicity by masking the antigen sites. The chondroitins sulfate make the collagen hemocompatible by reducing the aggregation of platelets and release of serotonin.

The chondroitins 6- and 4-sulfate used in the present invention, at the same time as the chitosan, as specified above, are advantageously associated with hyaluronic acid described above which plays a role of regulating cell growth and cell migration. Hyaluronic acid is the only unsulfated glycosaminoglycan.

It is a unit polymer: glucuronyl (beta 1,3)N-acetyl-galactosamine sulfate (beta 1,4). Hyaluronic acid has a molecular weight varying between 100,000 and several million depending on the tissue considered.

It should be emphasized that the introduction into formulations with a base of collagen and chondroitins sulfate, of chitosan, besides the improvements that it imparts to the dermis on the biological plane, contributes a solution to the problem of salting out and of crosslinking. Actually, this polysaccharide exhibits very numerous ionizable amino functions able to be bonded by ionic bond to each of the constituents of the dermis since they all exhibit (carboxylic and sulfonic) acid functions in considerable proportion.

In this case, and contrary to what happens after chemical crosslinking of collagen alone in known collagen-GAG mixtures, all the constituents are bonded together by a sufficiently great number of ionic bonds for the salting out to be negligible. The chemical composition of the dermes obtained remains invariable during operations requiring an immersion in aqueous solutions. The presence of chitosan in the dermal equivalents according to the invention therefore makes it possible to obtain a material with a very definite composition and which exhibits the feature of being insoluble in the fluids of the organism without it being necessary to resort to a covalent chemical crosslinking.

Further, the pseudoepidermal layer covering the artificial dermes should have physicochemical properties close to natural epidermes. This layer should act as the hydric flow regulator and as a barrier to infectious agents. Further, by its mechanical properties is should impart to the dermis-epidermis unit a solidity and elasticity compatible with the handling conditions occurring at the time of the graft (hydration, washing, cutting, suture...).

According to the invention, this layer consists of a film of chitosan or associated with chondroitins sulfate and/or collagen. It can also consist of these elements alone or associated with modified structure proteins such as carboxylmethyl or aminoethyl kerateins that are substituted.

The dermal layer comprises between 10 and 20% of chitosan, between 4 and 10% of chondroitins 4- and 6-sulfate, the percentages being calculated relative to the weight of the collagen.

The use of other polyelectrolytes in association with one or more of the ionizable macromolecules is possible. In particularly vegetable polyosides (polygalacturonic acid...) or polyamino acids can be used for the constitution of the ionic networks exhibiting the desired physicochemical properties.

These composite films are made more or less lipophilic by chemical grafting of nontoxic substituents such as fatty acids or other hydrophobic substances, or by surface application of a sebum substitute containing free or esterified fatty acids or other substance contained in the sebum.

The pseudoepidermes according to the invention offering the advantage relative to chemical substances generally used for making dermes impermeable, exhibit a lipophily that can be modulated as a function of the nature of the fatty substances used or the nature of the lipophilic substituents introduced.

DETAILED DESCRIPTION OF THE INVENTION

This invention will be better understood and its advantages will come out from the following examples which illustrate it without limiting it in any way.

In all the examples the chitosan is obtained by N-deacetylation of microfibrillar chitin (poly-N-acetylqlucosamine) coming from shrimp carapaces. It is a chitosan whose degree of cetylation is between about 10 and about 40%.

EXAMPLE 1

Preparation of the Dermis Making up the Essential Part of Artificial Skin

Preparation of the collagen solution:

The preferred collagens belong to type III+I, to type III, to type I, to type IV and to type V and are in the native form or without telopeptides, with preserved helicoidal structure, in solution or in fibrous form.

They are prepared, in a standard way, from calf dermis (collagens marketed in France by the S.A. de Developpement et d'Utilisation du Cuir). They can also be obtained from human placenta (collagens marketed in France by the Institut Merieux).

The solution is made by mixing, with a stirrer, 1% of collagen (weight/volume) in 0.05 M acetic acid at ambient temperature and pH 3.5.

If a less rigid dermis is desired, the concentration of the solution can be lowered to 0.3% (weight/volume).

Addition of chitosan:

The chitosan is prepared by N-deacetylation of microfibrillar chitin (poly-N-acetylglucosamine) coming from shrimp carapaces.

The chitosan thus obtained and highly purified is added to the preceding solution at a rate of 15% (weight/weight) relative to the collagen.

Besides its natural properties, chitosan acts as an ionic crosslinking agent. Its molecular can vary from 150,000 to 1,000,000.

The degree of acetylation, which can be made to vary from 40 to 10%, determines the degree of crosslinking and therefore makes it possible to act on the rate of degradation of the artificial skin.

Addition of Chondroitins Sulfate:

A mixture of chondroitins 4- and 6-sulfate purified to 99% from sheep nasal septa is then added to the collagen-chitosan solution at a rate of 6% (weight/weight) relative to the amount of initial collagen. The presence of the first two components facilitates the solubilizing of the GAGs which are quickly dissolved with stirring at ambient temperature.

At this stage, it is possible to add hyaluronic acid to the preceding solution at a rate of 1% (weight/weight) relative to the collagen This product makes possible an improvement of the cell adhesion and also makes it possible to improve cell growth more, which has already been promoted by the glycosaminoglycans.

Neutralization:

When a well-homogenized mixture of the different constituents has been obtained, neutralization of the dermis is performed. NaOH The pH is then brought to 6.5-7 by an N solution of or by a tris-HCl buffer (pH 10.5).

Another method consists in performing the neutralization after freeze-drying the solution. The dermis should then be rinsed in two successive baths of sterile water, physiological serum or tris-HCl buffer.

Lyophilization

The homogeneous solution obtained is lyophilized in industrial lyophilizing agents.

The thickness of the dermis depends on the amount of solution poured into the molds and can be adapted to the needs of the users. On an average, this thickness varies from 1 to 8 mm depending on the use.

It is also possible to make films, from the previously prepared homogeneous solution.

This solution is poured into molds and kept in an oven at 35° C. for 48 hours, which makes it possible to obtain a smooth, transparent artificial skin 0.1 to 0.8 mm thick.

Sterilization:

Two main sterilization processes are considered:
70° alcohol
gamma rays.

70° alcohol:

The artificial dermes are packaged in plastic bags filled with 70° alcohol according to standard techniques avoiding bacterial contamination to the maximum; all bacteriological tests made between a week and six months after packaging in alcohol proved to be negative.

Gamma radiation:

The artificial dermes can also be sterilized by ionizing irradiations. The gamma rays come from a cobalt 60 source.

The radiation dose can range from 1 to 3 megarads without deterioration of the properties of the dermis.

The artificial dermis thus obtained is subjected to different checks which will be set forth below. Some of these checks are represented in the accompanying diagrammatic drawing in which.

Figure 1:
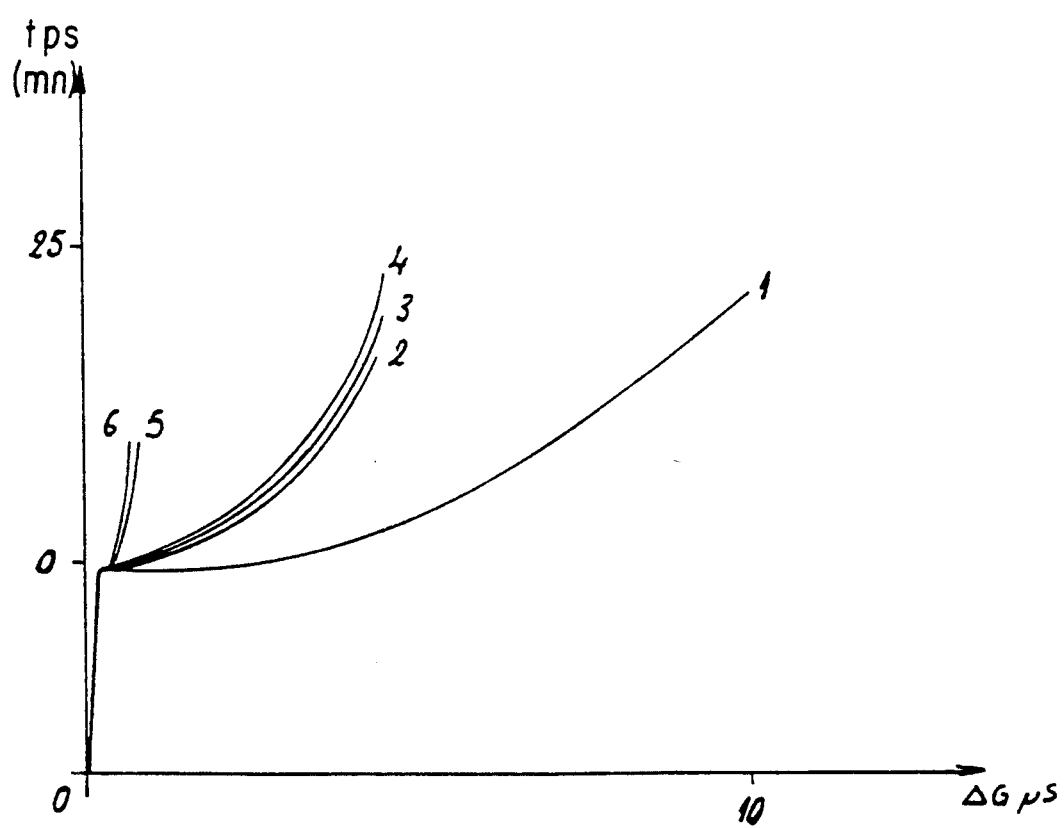
FIG. 1 is a curve representing the rate of enzymatic degradation of the dermis according to the invention by collagenase.

Electronic Microscopy:

Scanning electronic microscopy makes it possible to observe the porous structure of freeze-dried dermes, the lamellar structure of film-forming dermes, and to check the size of pores determined by the percentage of dry material of the dermis.

Transmission electronic microscopy makes it possible to display the microfibrillar structure of the dermis according to the invention.

Mechanical Properties of the Artificial Dermis:

Tensile strength tests of the material s were made on the ADAMEL LHOMERGY DY 21b measuring apparatus. The samples were prepared in the shape of dumbbells 0.05 cm wide and 3 cm long and 0.33 mm thick. Each end of the test piece is tightly clamped between the jaws of the apparatus.

The stretching measurements are performed at a rate of 5 or 10 mm/minute depending on the samples. Three tests are made for each measurement. The results are given in Table I below.

TABLE I

| Samples | Sterilization | Force DaN | Elongation (mm) | Young's Modul $Kg/cm^2$ |
|---|---|---|---|---|
| Collagen | Unsterile | 0.01 | Very slight | / |
| Collagen + GAG | Unsterile | 0.02 | Very slight | / |
| Collagen H + Ch + GAG | Unsterile | 0.9 | 14.33 | 0.16 |
| Collagen H + Ch + GAG | Gamma rays | 0.1 | 17.3 | 0.14 |
| Collagen H + Ch + GAG | Alcohol 70° | 0.09 | 15.7 | 0.145 |
| Collagen H + Ch + GAG + biodegradable pseudoepidermis | Alcohol 70° | 0.23 | 20.1 | 0.29 |
| Collagen B + Ch + GAG | Unsterile | 0.06 | 12.27 | 0.13 |
| Collagen B + Ch + GAG | Gamma rays | 0.07 | 13.00 | 0.13 |
| Collagen B + Ch + GAG | Alcohol 70° | 0.06 | 13.3 | 0.12 |

Collagen H: Human collagen
Collagen B: Bovine collagen
Ch: chitosan
GAG: glycosaminoglycans Comparison of the samples consisting of collagen alone, of collagen and glycosaminoglycans, and of collagen, chitosan and glycosaminoglycans shows that the presence of chitosan considerably increases the mechanical strength of the artificial dermis.

As can be seen, incorporation of 15% by weight of chitosan multiplies by four the force necessary to obtain the rupture of the compound. This clearly shows the cohesion force of the three molecules among themselves.

Study of the Rate of Enzymatic Degradation of Artificial Dermis by Collagenase:

The conductimetric measurements were made by the following technique:

4 ml of a sample suspension in trisCaCl$_2$ ImM pH 8 are placed in a thermostated cell at 30° C.

The conductance is registered by to a WAYNE-KERR B 641 transformer measuring bridge as soon as the thermal stability is reached (at the end of about ten minutes). The enzyme (collagenase of clostridium histolyticum EC 34 243—Sigma Number C-0773) is then introduced into the cell (final concentration of enzyme: 3.24 U/mlO and the variation of the conductance is recorded.

The enzymatic reaction is standardized by addition of a small volume (50 microliters) of 10 M HCl. The variations of conductance due to hydrolysis are then converted into the equivalent of freed protons in the medium by enzymatic reaction. The rate of hydrolysis is expressed in the equivalent of freed protons per liter and per hour (H/l/h).

TABLE II

| Sample | Sterilization | % Enzyme activity | Rate of degradation in $\mu m$ (H$^+$/1/h) |
|---|---|---|---|
| Human collagen | Unsterile | 100 | 1050 |

TABLE II-continued

| Sample | Sterilization | % Enzyme activity | Rate of degradation in μm (H+/1/h) |
|---|---|---|---|
| Collagen H + Ch + GAG (2) | Unsterile | 44.8 | 462 |
| Collagen H + Ch + GAG (3) | Gamma Rays | 32.2 | 402 |
| Collagen H + Ch + GAG (4) | Alcohol 70° | 38.9 | 340 |
| GAG (5) | Unsterile | 0 | 0 |
| Chitosan (6) | Unsterile | 0 | 0 |

Addition of chitosan and of GAG reduces by half the degradation of collagen by collagenase. There is no significant difference between the unsterile artificial dermis and that sterilized with qamma rays or 70° alcohol.

Study of X-Ray Diffraction:

This study makes it possible to check the integrity of the collagen molecule after production of the artificial dermis and after sterilization.

The samples are prepared with a hollow punch and flattened to obtain pellets 1 cm in diameter and 1 mm in thickness. These pellets are placed in an X-ray diffraction apparatus connected to a data-processing system.

Figure 2:
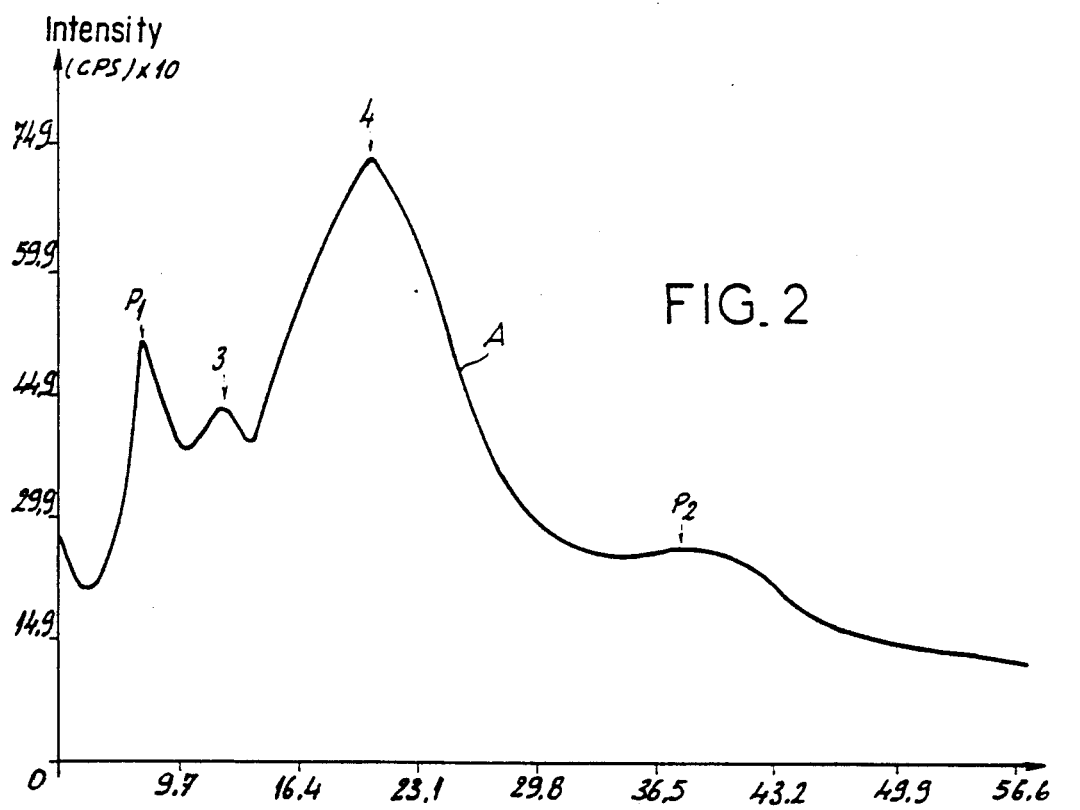
FIG. 2 represents the X-ray diffraction spectrum of collagen alone.
Figure 3:
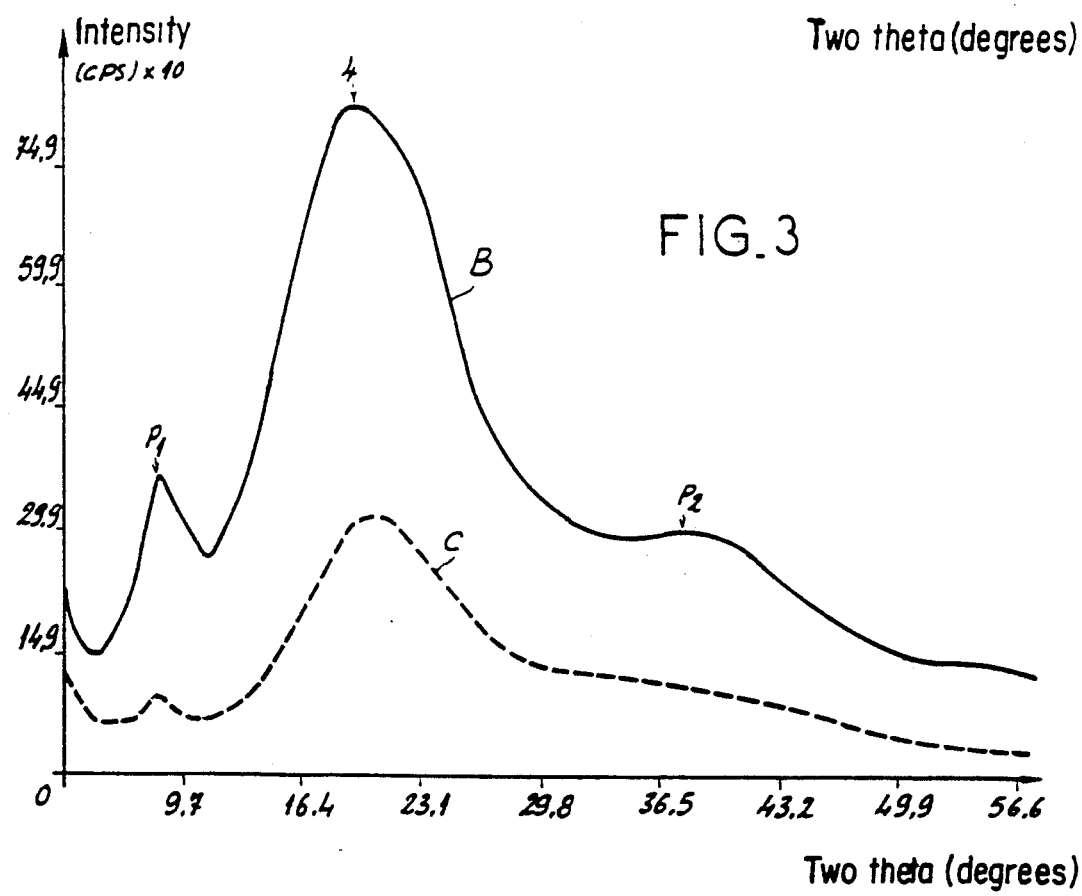
FIG. 3 represents the X-ray diffraction spectrum of the artificial dermis according to the invention, of a denatured collagen.
Figure 4:
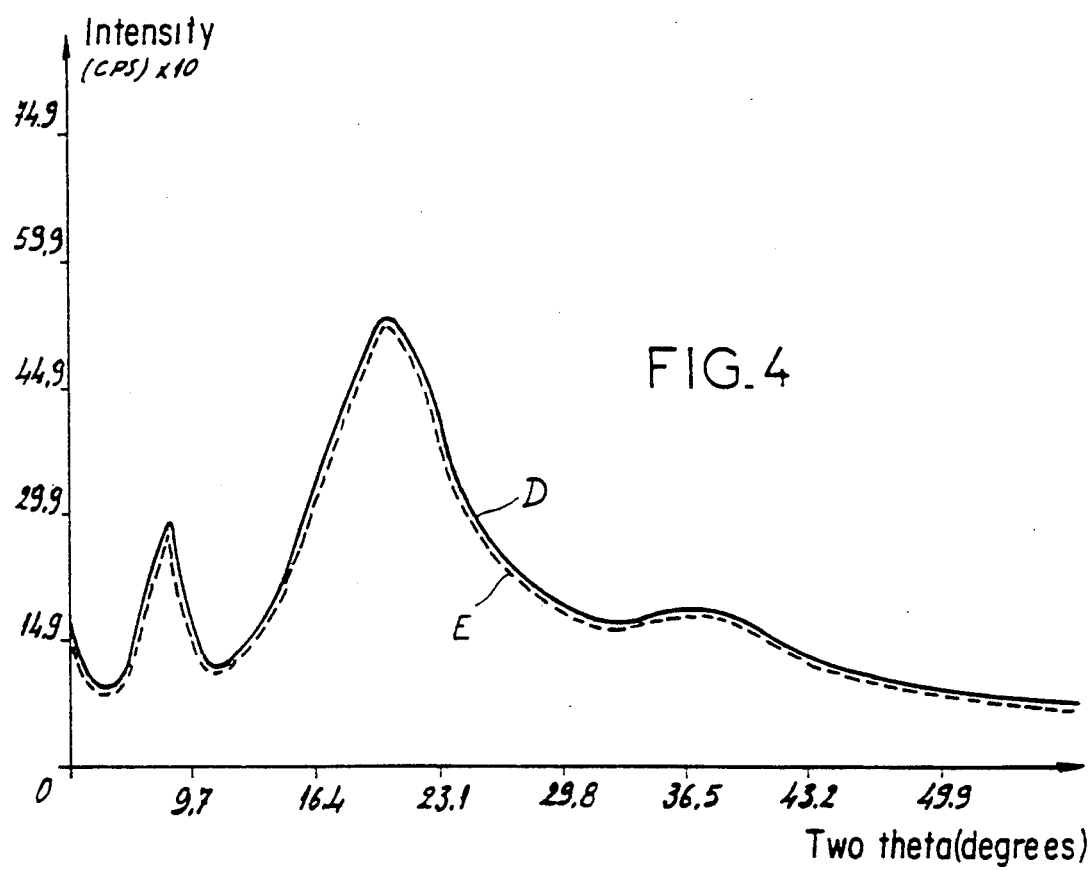
FIG. 4 represents the X-ray diffraction spectrum of the artificial dermis according to the invention once sterilized with X rays and 70° alcohol.

The results are given in FIGS. 2 to 4.

Peaks $P_1$ and $P_2$ characteristic of the collagen can be observed on curve A represented in FIG. 2.

Peak $P_1$ makes it possible to determine the distance between the collagen molecules. Peak $P_2$ reflects the distance between two acid molecules. Its presence makes it possible to determine the degree of integrity of the collagen molecule.

Peak 3 makes it possible to know the pitch of the helices of the collagen molecule. It is a peak particularly difficult to display.

Peak 4 cannot be used because it is given by all the amorphous elements contained in the artificial dermis.

In FIG. 3, curve B is that of the dermis according to the invention and curve C is that of the denatured collagen. It can be seen the production process does not alter the collagen molecule, since peak $P_2$ is always present.

Peak 3 is no longer visible. It seems to be masked by the residues of the chitosan and glycosaminoglycans.

Peaks $P_1$ deeps an identical amplitude in the artificial dermis and in the collagen alone.

The X-ray diffraction spectra observed in FIG. 4 show that the sterilization processes do not alter the collagen molecule either. In FIG. 4, curve D is that of the dermis sterilized with X rays, and curve E is that of the dermis sterilized with the 70° alcohol.

Electrophoreses:

A first series of electrophoreses on polyacrylamide gel in presence of SDS was performed. It makes it possible to separate the chains as a function of their molecular weight.

Figure 5:
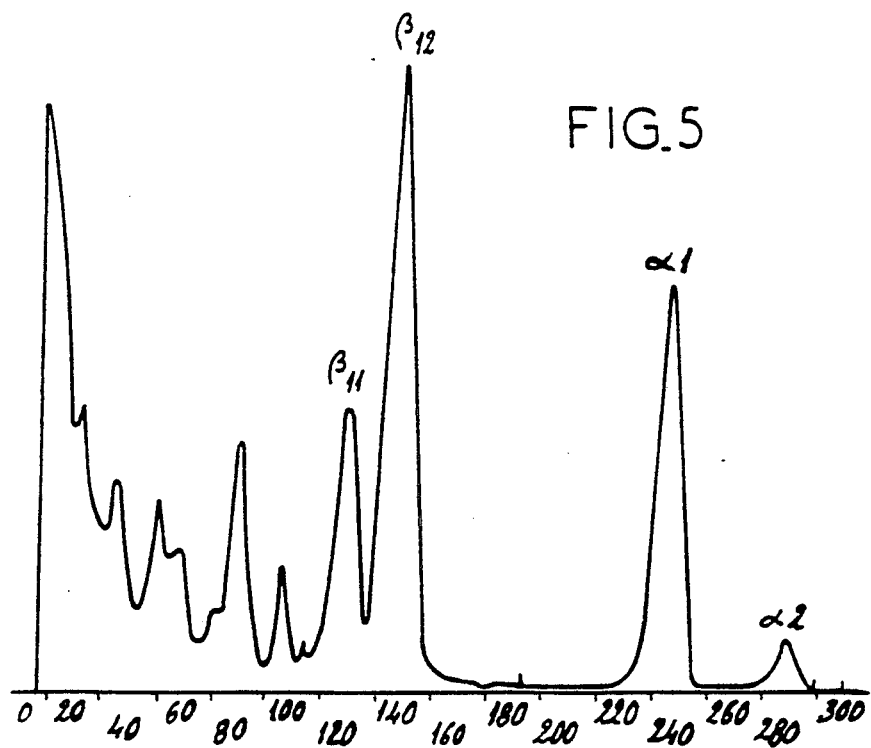
FIG. 5 represents the results of electrophoresis on a dermis made from bovine collagen.

The results of electrophoresis of the artificial dermis obtained from bovine collagen are collected in FIG. 5. The peaks $alpha_1$, $alpha_2$, $beta_{11}$, $beta_{12}$, characteristic of an acid-soluble bovine collagen, are present and are entirely comparable with a bovine collagen alone. The absence of peak corresponding to molecules of low molecular weight confirms that the production therefore does not alter the collagen molecules, which the X-ray diffraction study had already made it possible to assume.

Study of the Cytotoxicity:

A study of the direct and indirect cytotoxicity of the artificial dermis according to the invention on the cultures of fibroblasts and keratinocytes was performed. The results are given in Table III.

In each case, no sign of cytotoxicity was observed.

The morphology of the cells remains identical with that of the controls. The growth rate is slightly increased.

TABLE III

| Sample | Cytotoxicity Direct | Cytotoxicity Indirect | Speed of cell Growth |
|---|---|---|---|
| Control without artificial dermis | / | / | Normal |
| Collagen H + Ch + GAG sterilized with alcohol | Negative | Negative | Normal |
| Collagen H + Ch + GAG sterilized with gamma rays | Negative | Negative | Normal |
| Collagen B + Ch + GAG sterilized with alcohol | Negative | Negative | Normal |
| Collagen B + Ch + GAG sterilized with gamma rays | Negative | Negative | Normal |

Study of the Biocompatability of the Artificial Dermis:

The sterile artificial dermes are rinsed in two baths of physiological serum and cut to the desired dimensions with sterile surgical equipment.

The selected animal (white laboratory rat) is anesthetized by exposure to a mixture of oxygen and halothane.

Its back is shaved and washed with an antiseptic solution. Two excisions of 2 $cm^2$ are made to the back muscle of the animal with a minimum of bleeding. One receives artificial dermis, the other is used as a control.

A plug is sutured onto each wound and the whole is covered with a bandage.

Several series of three rats are made on this model.

The animals are sacrificed at day 2, day 7, day 15, day 21 and day 30.

The appearance of the artificial dermis is then noted, a biopsy is taken of the muscle in the two wounds for study with scanning and transmission electronic microscopy as well as their histological study.

The animal's blood is taken by intracardiac puncture for antibody research.

The results obtained on day 2 show a normal inflammatory reaction followed on day 7 by a cell colonization of artificial dermis. On day 15, no superinfection was observed.

The first results obtained at day 21 show that the artificial dermis is still present and is well colonized by the ells.

The artificial dermis thus obtained can be epidermized in a second period with a biodegradable pseudoepidermis; according to the invention, preferably a pseudoepidermis is used with a base of chitosan alone or associated with chondroitins sulfate and/or collaqen, and optionally with modified structure proteins or with other polyelectrolytes.

A certain lipophily is advantageously imparted to the pseudoepidermis by chemical grafting or by surface application of sebum substitute.

The dermis+pseudoepidermis composite material thus achieved exhibits all the advantages listed above. Further, it is entirely biodegradable and can be used as a support for the keratinocytes of the patient and be implanted in the days following burns.

Valuable relay in the techniques of early excision of 3rd degree burned tissue, it makes possible an immediate covering, avoid exudative and calorico-nitrogen losses, exhibits a barrier to infections, limits hydrotrophic cicatrices and crippling retractile sequellae. Further, it is an excellent support making it possible to consider the culture of epidermal cells on the patient himself.

Thus, the reconstitution of the epidermal layer will be formed at the same time as that of the dermal layer, a solution long awaited by all burn centers.

EXAMPLE 2

Embodiment of an Extracellular Matrix Favoring the Growth of Nerve Cells

A 1% (w/v) solution of collagen in 0.05 N acetic acid is achieved by stirring with a vertical stirrer. When the solution is quite homogeneous, 0.15% of chitosan, then 0.06% of glycosaminoglycans dissolved.

The solution obtained, which has the same concentrations the artificial dermis is poured into biocompatible silicone tubes with a diameter between 2 and 6 mm. These tubes are freeze-dried then sterilized with 70° alcohol or gamma rays.

These tubes are provided, in a first period, to be implanted in a rabbit to test the possibilities of regeneration of the sciatic nerve.

EXAMPLE 3

Embodiment of an Extracellular Matrix for Regeneration of Bone Tissue

A 1% (w/v) solution of chitosan in 0.05 N acetic acid is achieved according to the method described in example 1. To this solution are added 16% of collagen relative to the initial weight chitosan, then 84% of glycosaminoglycans (still relative to chitosan).

A precipitate is produced which is accentuated by bringing the pH to a threshold close to neutrality. This fibrous precipitate is recovered, pressed and placed in biocompatible silicone tubes of 0.9 to' 1.5 cm in diameter. A hole of 1 to 2 mm in diameter is made in the center of these tubes. It can be left as it is or filled with a solution of collagen (1%), chitosan (0.15%), glycosaminoglycans (0.06%), or concentrations of artificial dermis.

The silicone tubes are then dried in an oven or freeze-dried. Their appearance is then hard and fibrous. They are sterilized with gamma rays or 70° alcohol. These tubes, in a first period, are provided to be implanted in a rabbit or dog for studying the possibilities of regeneration and repair of bones or fragments of injured bones.

Calcium can be added to the initial mixture to come still closer to the normal bone structure.

EXAMPLE 4

Use of the Previously Described Mixtures to Achieve Biocompatible Envelopes of Already Existing Prostheses Silicone prostheses (mammary prostheses, chin protheses...) or Dacron prostheses (ligaments) are not recolonized by cells or are recolonized very slowly. This causes risks of more or less great slipping of silicone prostheses, particularly mammary prostheses.

A biocompatible material enveloping these prostheses will make possible the regeneration of a tissue which would prevent this slipping and would constitute an excellent interface of prostheses and surrounding tissues.

Embodiment of Biocompatible Envelopes:

A solution of collagen, chitosan and glycosaminoglycans is made under the conditions of example 3. The proportions of each constituent vary according to the shape and size of the prosthesis to be covered. On an average, the optimal proportions are: collagen 0.5% (w/v), chitosan 0.08% and glycosaminoglycans 0.03%.

The solution is degassed in a centrifuge (three fourths of an hour at 3000 rpm) then the resulting homogeneous liquid is spread over the entire surface of the prosthesis and put in an at 30° C. until complete drying is obtained.

The prosthesis and its envelope are then sterilized with alcohol or gamma rays.

EXAMPLE 5

Use of the Various Extracellular Matrices Described in Examples 1 to 3 as Cell Culture Support for Pharmacotoxicological Tests The solution described in examples 1 to 3 is poured into bottles, Petri dishes or multiwell plates and dried in an oven at 30° C. The formed film adheres to the dish and represents an excellent support for cell cultures.

On the other hand, the freeze-dried matrices can be used in vitro making it possible to achieve three-dimensional cultures of cells (fibroblasts, keratinocytes, chondrocytes...).

These culture models can serve for pharmacotoxicological study of different chemical or medicinal molecules.

In the pharmaceutical industries, these models are increasingly used because they make it possible to perform a screening of molecular families and to reduce considerably the use of laboratory animals.

We claim:

1. A biomaterial comprising an extracellular matrix for cellular colonization, said matrix comprising collagen, the amino and carboxyl groups of said collagen remaining ionically intact; a chitosan having a degree of acetylation of not more than 40%; and a glycosaminoglycan; said collagen, said chitosan, and said glycosaminoglycan being directly crosslinked one to another into a three-demensional ionic network bonding the amino groups of said collagen and said chitosan with the carboxyl groups of said collagen and said glycosaminoglycan and with the sulfate groups of said glycosaminoglycan.

2. A biomaterial according to claim 1 wherein the chitosan is obtained from N-deacetylation of microfibrillar chitin of shrimp carapaces.

3. A biomaterial according to claim 1 wherein the chitosan has a molecular weight of between 150,000 and 1,000,000.

4. A biomaterial according to claim 1 wherein the collagen is selected from the group consisting of type III+I, type III, type I, type IV, and type V collagens.

5. A biomaterial according to claim 1 wherein the glycosaminoglycan is selected from the group consisting of chondroitin 4-sulfate and chondroitin 6-sulfate.

6. A biomaterial according to claim 5 wherein said extracellular matrix is made of another glycosaminoglycan.

7. A biomaterial according to claim 6 wherein said another glycosaminoglycan is hyaluronic acid.

8. A biomaterial according to claim 1 wherein said extracellular matrix comprises between 10 and 2-% of chitosan, between 4 and 10% of glycosaminoglycan, these percentages being calculated relative to the weight of collagen.

9. A biomaterial according to claim 1 wherein the degree of acetylation of chitosan is between 10 and 40%.

10. A substitute bone tissue comprising a biomaterial according to claim 1.

11. A biocompatible envelope comprising a biomaterial according to claim 1.

12. A substitute skin comprising a dermal layer comprising a biomaterial according to claim 1.

13. A substitute skin according to claim 12 comprising a biodegradable pseudoepidermis with a membrane structure lying over the dermal layer.

14. A substitute skin according to claim 13 wherein the pseudoepidermis comprises chitosan.

15. A substitute skin according to claim 13 wherein the pseudoepidermis comprises a compound selected from the group consisting of chondroitin sulfate and collagen.

16. A substitute skin according to claim 13 wherein the pseudoepidermis comprises a protein structure selected from the group consisting of carboxymethylkeratin and aminoethylkeratin.

17. A method for preparing the biomaterial according to claim 1 comprising:
  dissolving collagen in an aqueous acidic medium to obtain a collagen solution;
  adding chitosan to said collagen solution to obtain a collagen-chitosan mixture;
  adding glycosaminoglycan to said mixture so as to obtain a final solution;
  removing said aqueous medium from said final solution, to obtain an extracellular matrix.

18. A biomaterial obtained by the method according to claim 17.

* * * * *